United States Patent
Lee et al.

(10) Patent No.: US 6,356,781 B1
(45) Date of Patent: Mar. 12, 2002

(54) FUNCTIONAL MAGNETIC RESONANCE IMAGING CAPABLE OF DETECTING THE OCCURRENCE OF NEURONAL EVENTS WITH HIGH TEMPORAL ACCURACY

(75) Inventors: Tso Ming Lee, Upper Saddle River; Seija Ogawa, Warren, both of NJ (US); Raymond Aaron Stepnoski, Doylestown, PA (US)

(73) Assignee: Lucent Technologies, Inc., Murray Hill, NJ (US)

( * ) Notice: Subject to any disclaimer, the term of this patent is extended or adjusted under 35 U.S.C. 154(b) by 0 days.

(21) Appl. No.: 09/540,823

(22) Filed: Mar. 31, 2000

(51) Int. Cl.$^7$ .................................................. A61B 5/00
(52) U.S. Cl. ........................................ 600/410; 324/309
(58) Field of Search .................................. 600/407, 410, 600/425, 555, 557, 558; 324/307, 309; 351/223, 239

(56) References Cited

U.S. PATENT DOCUMENTS

| | | | |
|---|---|---|---|
| 5,603,322 A | * | 2/1997 | Jesmanowicz et al. ... 128/653.2 |
| 5,632,276 A | * | 5/1997 | Eidelberg et al. ........ 128/653.1 |
| 6,018,675 A | * | 1/2000 | Apkarian et al. ............ 600/407 |
| 6,045,515 A | * | 4/2000 | Lawton ....................... 600/558 |
| 6,213,956 B1 | * | 4/2001 | Lawton ....................... 600/558 |

\* cited by examiner

Primary Examiner—Marvin M. Lateef
Assistant Examiner—Eleni Mantis Merlader
(74) Attorney, Agent, or Firm—DeMont & Breyer, LLC; Jason Paul DeMont; Wayne S. Breyer

(57) ABSTRACT

A method of detecting the occurrence of neuronal events in a brain with high temporal accuracy and of distinguishing between contemporaneous neuronal events is disclosed. In accordance with the illustrative embodiment of the present invention, two or more stimuli are chosen and administered to a subject at a temporal interval apart. Each stimulus causes a neuronal event in the brain of the subject, and if the two neuronal events occur at the same time and at the same place, they interfere, which interference is manifested by different physiological effects than are caused by either neuronal event alone. When the interference is detected, the time interval between the first stimulus and the second stimulus can be compared to a nominal range. If the time interval is outside of the nominal range, then it suggests that a pathological condition exists. The illustrative embodiment of the present invention comprises: stimulating a subject with a first stimulus to cause a first event in the subject; stimulating the subject with a second stimulus to cause a second event in the subject, wherein the second stimulus occurs at a temporal interval, $\Delta t_n$, after the first stimulus, and wherein the first event and the second event jointly affect at least one characteristic of a first physiological effect at a first region of the subject as a function of the temporal interval, $\Delta t_n$; and measuring the at least one characteristic of the first physiological effect at the first region of the subject.

21 Claims, 6 Drawing Sheets

FIG. 1
PRIOR ART

FIG. 2
PRIOR ART
(NOT TO SCALE)

FUNCTIONAL MAGNETIC RESONANCE IMAGING CAPABLE OF DETECTING THE OCCURRENCE OF NEURONAL EVENTS WITH HIGH TEMPORAL ACCURACY

FIELD OF THE INVENTION

The present invention relates to physiology, diagnostics, and neuroscience in general, and, more particularly, to functional magnetic resonance imaging, which is commonly known as "fMRI."

BACKGROUND OF THE INVENTION

The human brain comprises billions of neurons that interact in a manner that diagnosticians have long sought to fully understand. One fact that is known about the operation of the brain is that the brain responds to a stimulus with a cascade of neuronal events. For the purposes of this specification, a "stimulus" is defined as an agent, action, or condition, either internal or external, that elicits, inhibits, accelerates, or decelerates a physiological or psychological activity or response. A stimulus includes,.but is not limited to visual, audible, tactile, olfactory, sapid, electrical, and chemical input. For example, the brain can receive a stimulus through one of the sense organs or not, as in, for example, the case of neuro-pharmacological agents.

Figure 1:
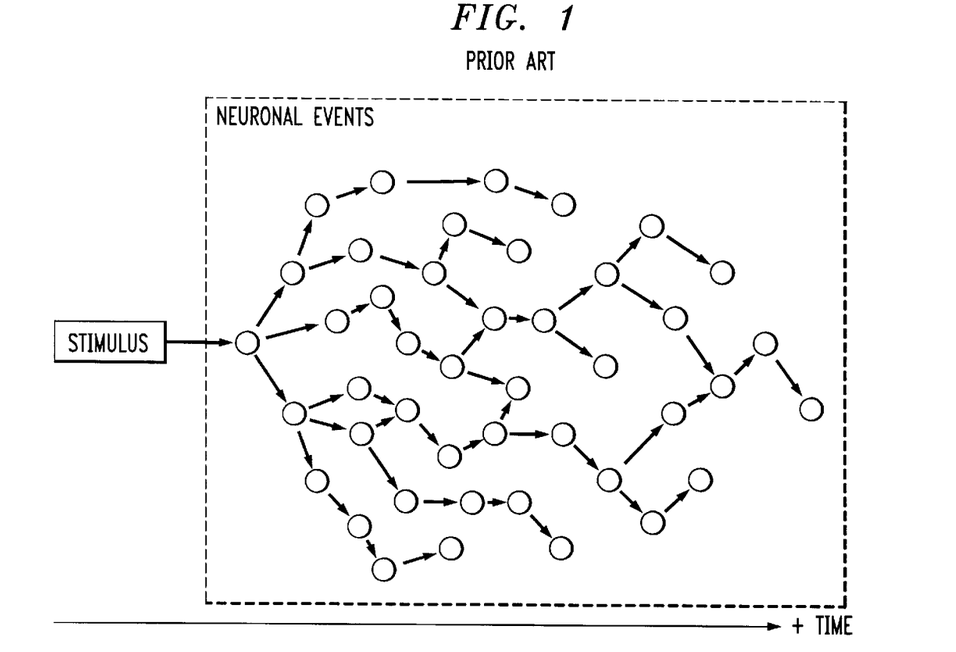
FIG. 1 depicts a diagram of a stimulus that triggers a cascade of neuronal events, as is well-known in the prior art.

FIG. 1 depicts a diagram of a stimulus that triggers a cascade of neuronal events, as is well-known in the prior art. As shown in FIG. 1, each neuronal event is represented by a circle, and each neuronal event is triggered by either: (i) the stimulus, (ii) another neuronal event, or (iii) the confluence of two or more neuronal events. Some neuronal events trigger other neuronal events and some do not. Although the cascade depicted in FIG. I comprises several dozen neuronal events, a typical cascade in the human brain in response to a typical stimulus comprises hundreds or thousands of neuronal events or more.

The topology of a cascade is causal, and, therefore, if the same stimulus is administered to one person under identical circumstances but at different times, the same cascade will occur. Furthermore, because the operation of the brain is considered to be at least partially the result of genetic factors—in contrast to wholly the result of environmental factors—it is hypothesized that if the same stimulus is administered to different people under similar circumstances, a similar cascade will be generated in both people. If true, this hypothesis is useful because it suggests that a variation in a person's observed cascade from the predicted cascade is an indication of a pathological condition in that person.

To determine whether a person's cascade is nominal or not, a diagnostician must be able to: (1) detect and identify each neuronal event that makes up a cascade, (2) detect the sequence (or relative timing) in which the neuronal events that make up the cascade occur, and (3) distinguish the neuronal events that make up the cascade from other contemporaneous neuronal events that are not part of the cascade.

Two well-known techniques for detecting neuronal events are electroencephalography (commonly known as "EEG") and magnetic encephalography (commonly known as "MEG"). Although these techniques are advantageous for detecting the existence and relative timing of temporally-disparate neuronal events, they are not well-suited for distinguishing between contemporaneous neuronal events.

As is well-known in the prior art, contemporaneous neuronal events can be distinguished from each other based on where in the brain they occur. For example, each neuronal event occurs not throughout the entire brain or at different places in the brain at different times but always at a specific spatially-defined region of the brain. In other words, each neuronal event always occurs in the same region of the brain each time it occurs and nowhere else. This fact is useful because it means that contemporaneous neuronal events can be distinguished based on where they occur (ie., on their spatial disparity).

Another well-known technique for studying brain activity is known as functional magnetic resonance imaging. The principal advantage of functional magnetic resonance imaging over electroencephalography and magnetic encephalography is that it is accurate at detecting whether a neuronal event has occurred at a specific region of the brain or not, and, therefore, it is well-suited to distinguishing between contemporaneous neuronal events.

On the other hand, functional magnetic resonance imaging is disadvantageous in comparison to electroencephalography and magnetic encephalography in several ways. First, it is laborious and slow to use functional magnetic resonance imaging to detect all of the neuronal events that make up a cascade. Second, functional magnetic resonance imaging is not well-suited for detecting the relative timing of neuronal events, which is necessary to ensure that the neuronal events in the cascade occur in the proper sequence. And third, functional magnetic resonance imaging does not directly detect a neuronal event, but only infers its occurrence by detecting some of its physiological effects. For example, a neuronal event at a region of the brain causes hemodynamic and metabolic effects at that region, and it is these hemodynamic and metabolic changes that the magnetic resonance imaging detects. For the purposes of this specification, the term "physiological effect" is defined as a function of a living organism or any of its parts, and explicitly includes: hemodynamic effects or metabolic effects or both. Although neuronal events are well defined temporally, their associated hemodynamic and metabolic effects are not well-defined temporally, and, therefore, it is difficult to precisely detect when a neuronal event occurs by observing either its hemodynamic or metabolic effects.

Figure 2:
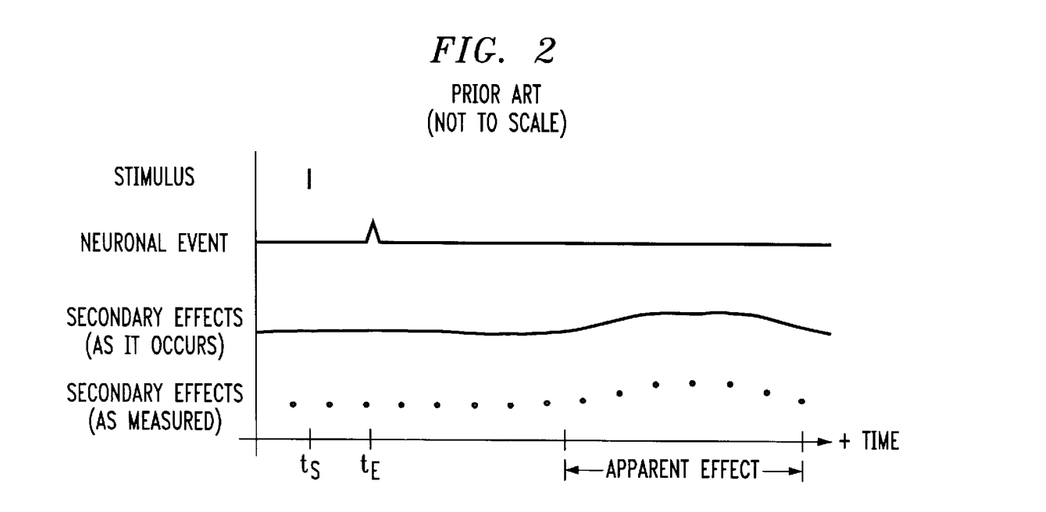
FIG. 2 depicts a time line that shows the temporal relationship of a stimulus to one neuronal event triggered (either directly or indirectly) by that stimulus and to the physiological effects associated with that neuronal event.

FIG. 2 depicts a time line that shows the temporal relationship of a stimulus to one of the many neuronal events triggered (either directly or indirectly) by that stimulus and to the hemodynamic and metabolic effects caused by that neuronal event. As shown in FIG. 2, a stimulus occurs at time $t=t_S$, which triggers a neuronal event at time $t=t_E$, which in turn causes an apparent physiological effect some time later. Although the neuronal event is temporally well defined and might last only a few milliseconds, the physiological effect is not temporally well defined and typically occurs many seconds after the neuronal event. Therefore, it is difficult to detect when a neuronal event occurs with high temporal accuracy by observing its physiological effects.

Another well-known technique for studying brain activity is positron emission tomography (commonly known as "PET") where a patient is injected with a $O^{15}$ water injection and neuronal events are detected by observing changes in regional cerebral blood flow (commonly known as "rCBF"). In this sense, positron emission tomography is similar to magnetic resonance imaging, but positron emission tomography does not enable diagnosticians to observe neuronal events in real time.

Therefore, the need exists for a technique that is capable of detecting the occurrence of neuronal events with high temporal accuracy and of distinguishing between contemporaneous neuronal events.

SUMMARY OF THE INVENTION

The present invention is a technique for studying brain activity that avoids some of the costs and disadvantages associated with techniques in the prior art. In particular, the illustrative embodiment of the present invention is a technique that is capable of detecting the occurrence of neuronal events in a brain with high temporal accuracy and of distinguishing between contemporaneous neuronal events. Furthermore, some embodiments of the present invention are advantageous in that they are noninvasive and enable the observation of neuronal events in real time. For these reasons, some embodiments of the present invention might be useful in medicine and neuroscientific research.

In accordance with the illustrative embodiment of the present invention, the brain activity of a subject is tested by observing whether one or more predicted neuronal events (that are part of a cascade of neuronal events triggered by a known stimulus under controlled conditions) do occur when and as expected. In other words, a known stimulus is administered to a subject under controlled conditions to trigger a predictable cascade of neuronal events. The subject is then observed using magnetic resonance imaging to determine when and if the predicted neuronal events do indeed occur. If they do not occur at all, or occur at times that are significantly different than expected, it might suggest a pathological condition in the subject. By performing a battery of such tests, the nature and location of the pathology might be determined.

To observe when and if a first neuronal event occurs as predicted, a cascade of neuronal events, which is expected to comprise the first neuronal event, is triggered by a first stimulus, in well-known fashion. Thereafter, the occurrence of the first neuronal event is inferred, in well-known fashion by using magnetic resonance imaging to detect the physiological effects of the first neuronal event. Although this alone does not determine when the first neuronal event occurred with high temporal accuracy, it does indicate whether a neuronal event is occurring or not at a particular region at approximately the predicted time. Furthermore, it provides a baseline of the physiological effects at that region at a given time with respect to the first stimulus.

Next, a second neuronal event is triggered by a second stimulus at a time interval before or after the first stimulus. Advantageously, the second stimulus and the time interval are chosen so that the second neuronal event and the first neuronal event occur at the same time and in the same region of the brain. If the first neuronal event and the second neuronal event do occur at the same time and at the same place, they will interfere, either constructively or destructively, which interference is manifested by different physiological effects than were caused by the first neuronal event alone (i.e., the baseline). In other words, the physiological effects at a region in response to one neuronal event are different than the physiological effects at the region in response to two interfering neuronal events. For example, one neuronal event may interfere with a second neuronal event by inhibiting the second neuronal event.

If the first neuronal event and the second neuronal event do not occur at the same time, there will be no interference, which is manifested by physiological effects that resemble the baseline. If the first neuronal event and the second neuronal event do not interfere, the time interval between the first stimulus and the second stimulus can be changed in an attempt to make them interfere. When the interference is detected, the time interval between the first stimulus and the second stimulus can be compared to a nominal range. If the time interval is outside of the nominal range, then it suggests that a pathological condition exists.

Because interference will only occur when the two short-lived and comparably well-defined neuronal events coincide in time, and will not occur if they are asynchronous, some embodiments of the present invention enable the detection of neuronal events with a high temporal resolution. And because magnetic resonance imaging equipment is used, it is easy to distinguish between, and to separately test, contemporaneous neuronal events.

The illustrative embodiment of the present invention comprises: stimulating a subject with a first stimulus to cause a first event in the subject; stimulating the subject with a second stimulus to cause a second event in the subject, wherein the second stimulus occurs at a temporal interval, $\Delta t_n$, after the first stimulus, and wherein the first event and the second event jointly affect at least one characteristic of a first physiological effect at a first region of the subject as a function of the temporal interval, $\Delta t_n$; and measuring the at least one characteristic of the first physiological effect at the first region of the subject.

DETAILED DESCRIPTION

Figure 3:
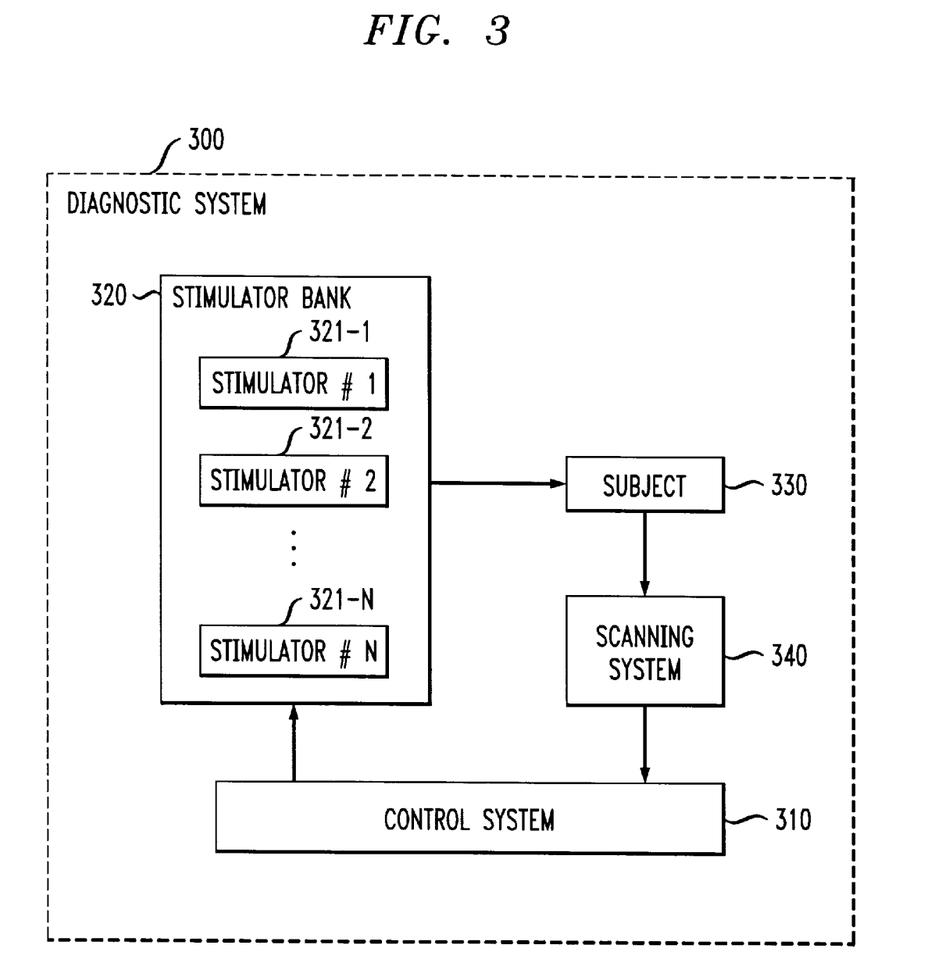
FIG. 3 depicts a block diagram of diagnostic system 300 in accordance with the illustrative embodiment of the present invention.

FIG. 3 depicts a block diagram of diagnostic system 300 in accordance with the illustrative embodiment of the present invention. Diagnostic system 300 comprises: control system 310, stimulator bank 320, subject 330 and scanning system 340, interconnected as shown.

Control system 310 comprises the computers and equipment needed to control stimulator bank 320 and to analyze the data from scanning system 340 about subject 330. Control system 310, stimulator bank 320, and scanning system 340 perform the functionality described below and depicted in FIG. 4.

Stimulator bank 320 comprises a plurality of N stimulators (stimulators 321-1 through 321-N) each of which is capable of stimulating subject 330 with a stimulus under the direction of control system 310. In particular, stimulator bank 320 is capable of multiple administrations of a series of two or more stimuli to subject 330 at precise and variable times. For example, control system 310 is advantageously capable of directing stimulator bank 320 to repeat the following series every ten seconds for 100 seconds: flash a red light into the left eye of subject 330 for 200 milliseconds followed 350 milliseconds later by a 440 Hz tone into the right ear of subject 330 for 1.700 seconds followed 300 milliseconds later by a mild electric shock to the left foot of subject 300. Each of stimulators 321-1 through 321-N is capable of stimulating subject 330 with a particular kind of stimulus.

Subject 330 is advantageously a living being, such as an animal, plant or human being.

Scanning system 340 is advantageously a magnetic resonance imaging system as is well-known to those skilled in the art and is capable of detecting one or more characteristics (e.g., magnitude, etc.) of one or more physiological effects at a first region of subject 330, and of providing the empirical data gathered to control system 310 for analysis. It will be clear to those skilled in the art how to make and use magnetic resonance imaging system 340.

Alternatively, scanning system 340 can be a positron emission tomography system, a near-infrared transcranial spectroscopy system, light computer tomography scan system as are well-known in the art. Such systems a might be manufactured by the Hamamatsu and the Hitachi Medical companies of Japan.

Figure 4:
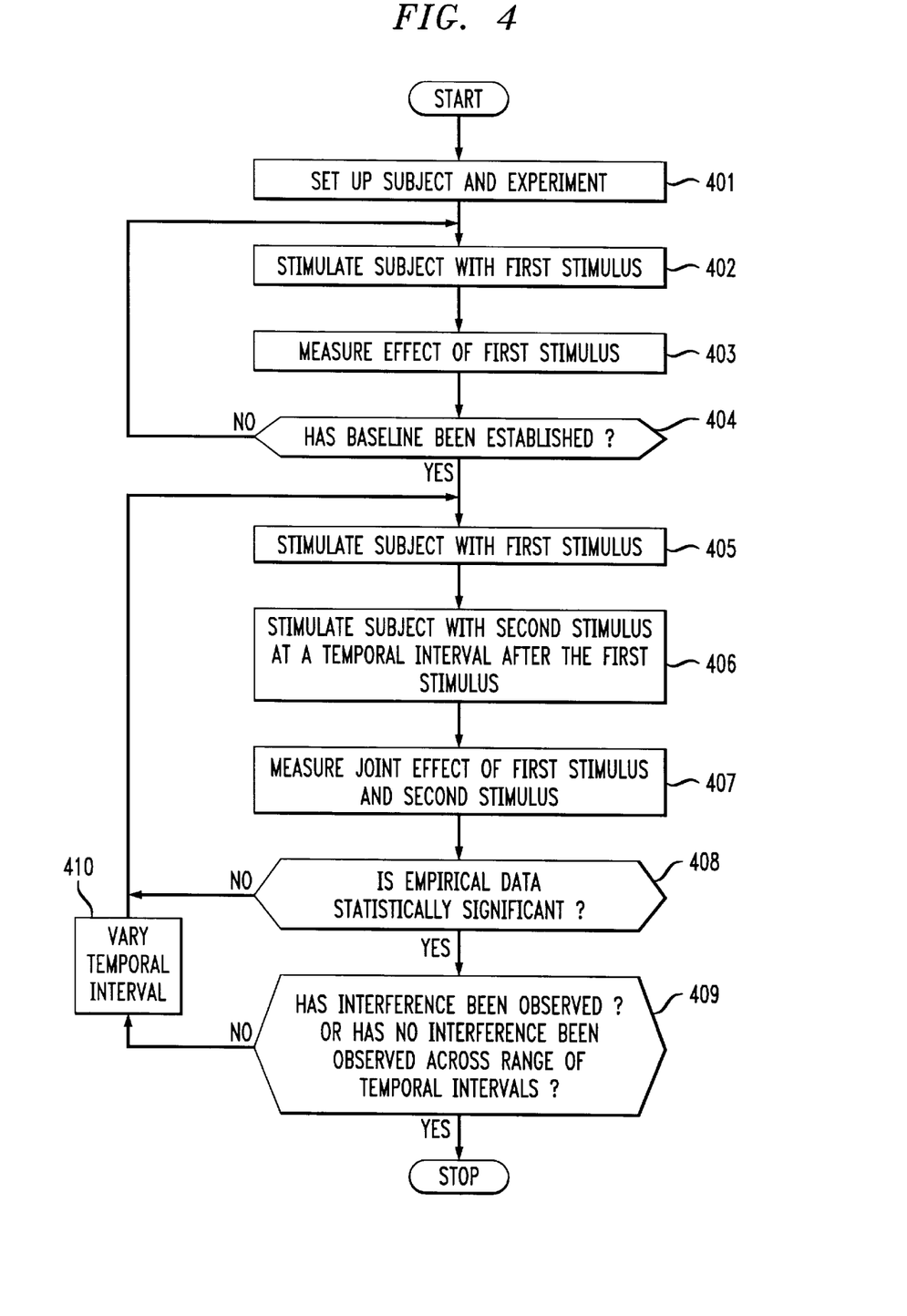
FIG. 4 depicts a flowchart of the operation of diagnostic system 300 in accordance with the illustrative embodiment of the present invention.

FIG. 4 depicts a flowchart of diagnostic system 300 in accordance with the illustrative embodiment of the present invention.

At step 401, the subject 330 of FIG. 3 is positioned within scanning system 340 and so that it can properly receive the stimuli administered by stimulator bank 320. Advantageously, subject 330 is prevented from receiving any external stimulus other than that provided by stimulator bank 320.

In steps 402 through 404, the illustrative embodiment stimulates subject 330 with a first stimulus so as to establish a baseline physiological response at the time and place of interest in subject 330, which baseline will be used as a benchmark against the data collected in steps 405 through 407.

At step 402, control system 310 directs a stimulator in stimulator bank 320 to stimulate subject 330 with a first stimulus to cause a first event (e.g., a neuronal event, etc.) in subject 330. As will be clear to those skilled in the art, the type of stimulus administered and its various characteristics is chosen depending on the type of subject being examined and the type of event that it is desired to observe.

At step 403, scanning system 340 measures at least one characteristic of a physiological effect that is caused by the event in step 402. For example, when the subject is a human being and the event is a neuronal event, scanning system 340 might measure the hemodynamic effect or metabolic effect or both at a region in the human being's brain. Typically, the region might be small (e.g., on the magnitude of a cubic millimeter or less, a dozen neurons, a single neuron, etc.) The empirical data gathered in step 403 is passed by scanning system 340 to control system 310.

At step 404, control system 310 repeats steps 402 and 403 either: (1) a fixed number of times, or (2) until a statistically significant baseline of empirical data is gathered.

At step 405, control system 310 directs a stimulator in stimulator bank 320 to stimulate subject 330 exactly as the first stimulus was administered in step 402.

At step 406, control system 310 directs a stimulator in stimulator bank 320 to stimulate subject 330 with a second stimulus to cause a second event in subject 330, wherein the second stimulus occurs at a temporal interval, $\Delta t_n$, after the first stimulus was last administered in step 405. For the purposes of this specification, the temporal interval can have a negative value, which means that the second stimulus occurs before the first stimulus. If the temporal interval has a positive value, it means that the second stimulus occurs after the first stimulus. The temporal interval can also be zero, which means that the first and second stimulus are concurrent.

Furthermore the first stimulus and the second stimulus can either be the same or they can be different.

At step 407, scanning system 340 measures at least the characteristics of the physiological effect that were measured in step 403. The empirical data gathered in step 407 is passed by scanning system 340 to control system 310.

At step 408, control system repeats steps 405, 406, and 407 either: (1) a fixed number of times, or (2) until the empirical data gathered in step 407 is statistically significant.

At step 409, control system 310 repeats steps 405, 406, and 407, each time varying the temporal interval until either: (1) a comparison of the data gathered in steps 403 and 407 indicates that an interference has been observed, or (2) a comparison of the data gathered in steps 403 and 407 across the range of temporal intervals indicates that no interference has been observed. If steps 405 through 407 are to be repeated with a different time interval, control system 310 executes step 410.

Figure 5:
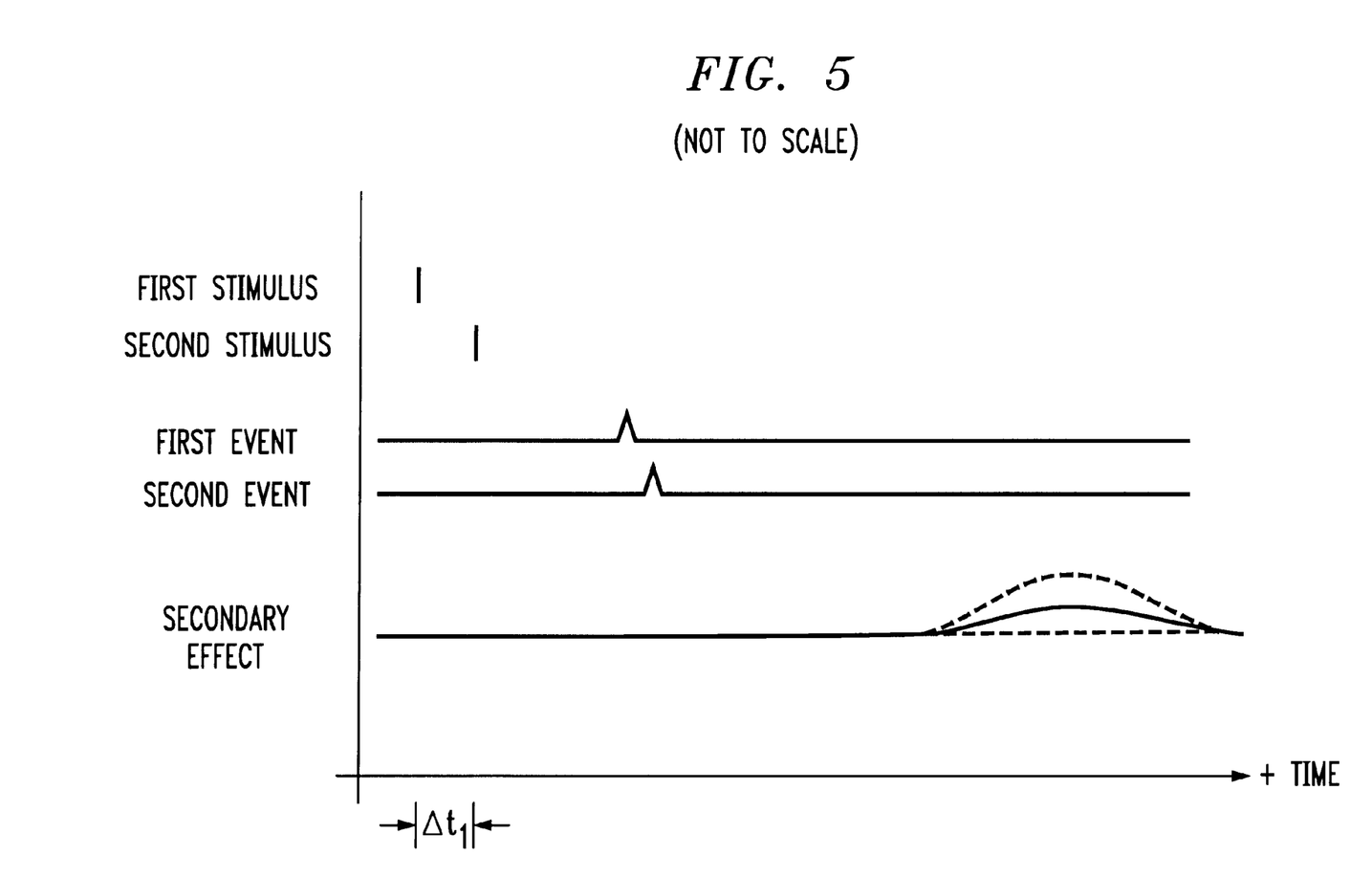
FIG. 5 depicts a timing diagram of an administration of a first stimulus and a second stimulus that are separated by a first time interval, $\Delta t_1$, that does not result in an apparent interference of the events caused by the first stimulus and the second stimulus.
Figure 6:
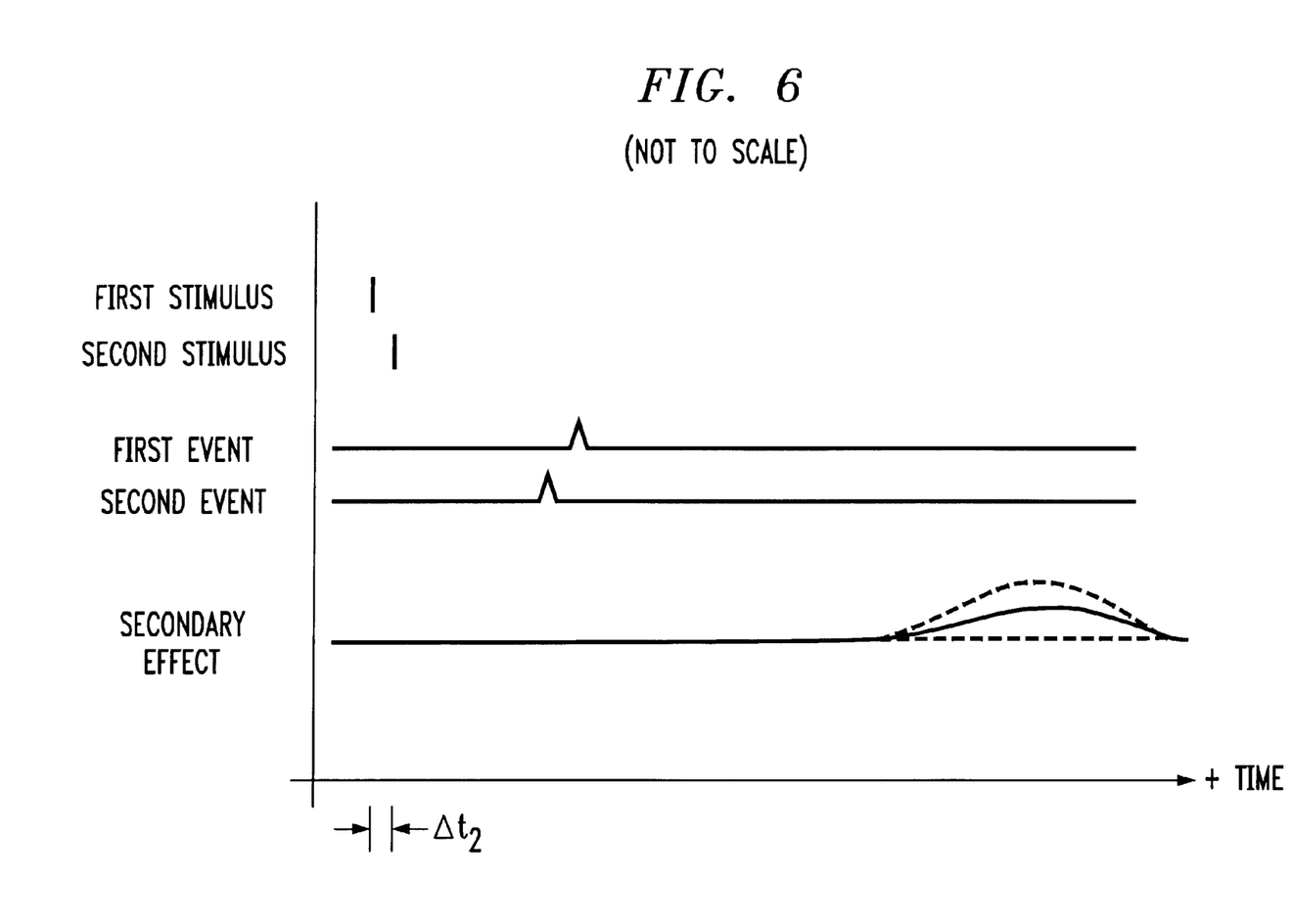
FIG. 6 depicts a timing diagram of an administration of a first stimulus and a second stimulus that are separated by a second time interval, $\Delta t_2$, that does not result in an apparent interference of the events caused by the first stimulus and the second stimulus.
Figure 7:
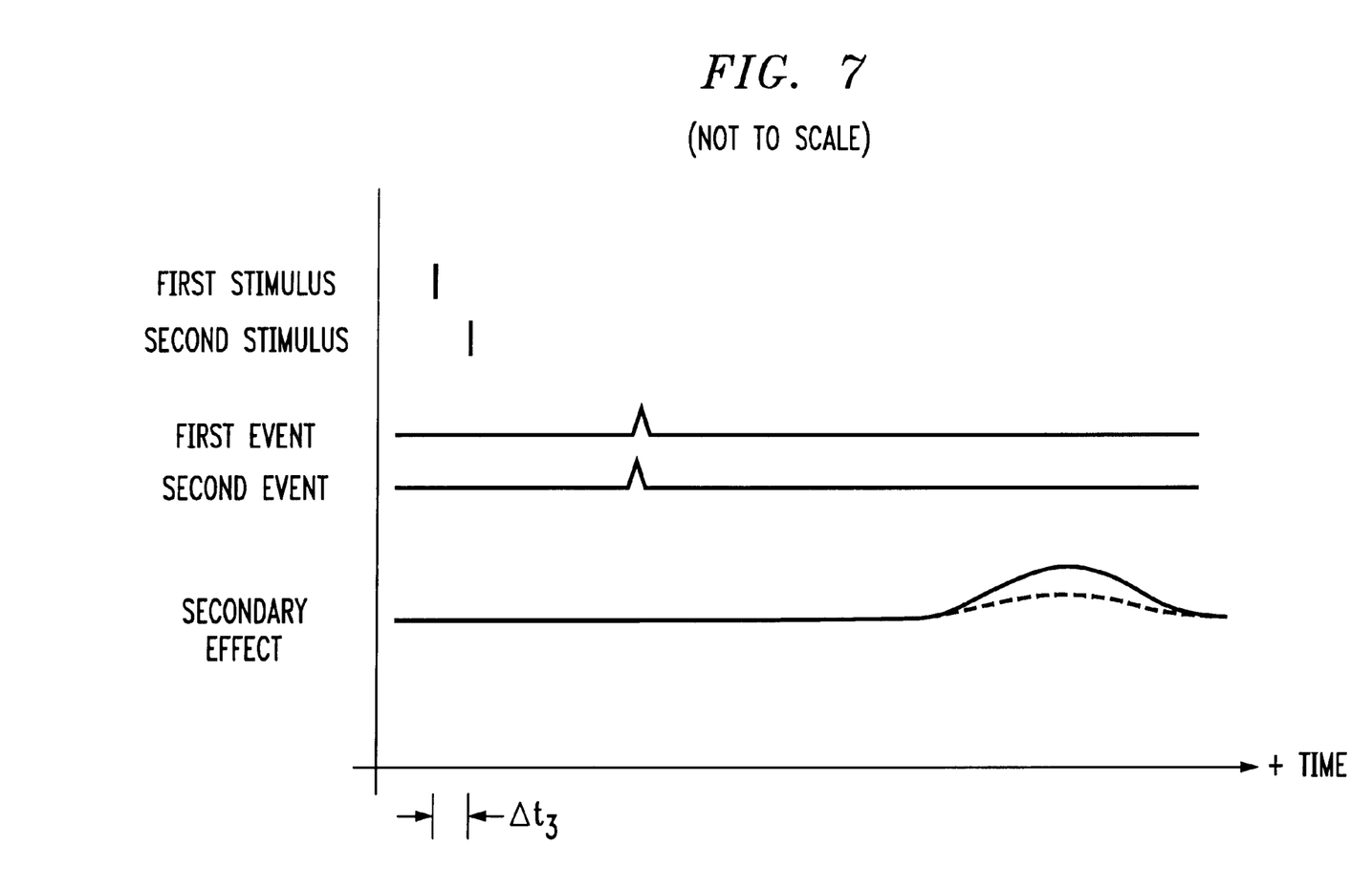
FIG. 7 depicts a timing diagram of an administration of a first stimulus and a second stimulus that are separated by a third time interval, $\Delta t_3$, that does result in an apparent interference of the events caused by the first stimulus and the second stimulus.

FIGS. 5, 6, and 7 depict three administrations of steps 405 through 407 that are identical in all respects except that the first stimulus and the second stimulus are separated by a different time interval, $\Delta t_n$. In FIG. 5 the temporal interval between the first stimulus and the second stimulus is too great, the first neuronal event precedes the second neuronal event, there is no apparent interference between the first neuronal event and the second neuronal event. The dotted line indicates what the secondary effect might look like if an interference had occurred.

In FIG. 6 the temporal interval between the first stimulus and the second stimulus is too small, which causes the first neuronal event to be preceded by the second neuronal event, and there is no apparent interference between the first neuronal event and the second neuronal event. Again, the dotted line indicates what the secondary effect might look like if an interference had occurred.

In FIG. 7 the temporal interval between the first stimulus and the second stimulus is such that the first neuronal event coincides with the second neuronal event as evidenced by the apparent interference between the first neuronal event and the second neuronal event. The dotted line indicates what the secondary effect might look like if an interference had not occurred.

TABLE 1

Summary of Observed Results for Different Temporal Intervals

| Figure | $\Delta t_n$ | Result |
| --- | --- | --- |
| FIG. 5 | $\Delta t_1$ | no apparent interference |
| FIG. 6 | $\Delta t_2$ | no apparent interference |
| FIG. 7 | $\Delta t_3$ | apparent interference |

It is to be understood that the above-described embodiments are merely illustrative of the present invention and that many variations of the above-described embodiments can be devised by those skilled in the art without departing from the scope of the invention. It is therefore intended that such variations be included within the scope of the following claims and their equivalents.

What is claimed is:

1. An apparatus comprising:
   means for stimulating a subject with a first stimulus to cause a first neuronal event in the subject;
   means for stimulating the subject with a second stimulus to cause a second neuronal event in the subject, wherein said second stimulus occurs at a temporal interval, $\Delta t_n$, after said first stimulus, and wherein said first neuronal event and said second neuronal event interfere to jointly affect at least one characteristic of a first physiological effect at a first region of the subject as a function of said temporal interval, $\Delta t_n$; and a magnetic resonance imaging system for measuring said at least one characteristic of said first physiological effect at said first region of the subject.

2. The apparatus of claim 1 wherein said means for stimulating a subject with a first stimulus and said means for stimulating the subject with a second stimulus are the same.

3. The apparatus of claim 1 wherein said means for stimulating a subject with a first stimulus and said means for stimulating the subject with a second stimulus are different.

4. The method of claim 1 wherein said first stimulus and said second stimulus are the same.

5. The method of claim 1 wherein said first stimulus and said second stimulus are different.

6. A method comprising:

stimulating a subject with a first stimulus to cause a first neuronal event in the subject;

stimulating the subject with a second stimulus to cause a second neuronal event in the subject, wherein said second stimulus occurs at a temporal interval, $\Delta t_n$, after said first stimulus, and wherein said first neuronal event and said second neuronal event interfere to jointly affect at least one characteristic of a first physiological effect at a first region of the subject as a function of said temporal interval, $\Delta t_n$; and measuring said at least one characteristic of said first physiological effect at said first region of the subject.

7. The method of claim 1 further comprising:

stimulating the subject with a second instance of said first stimulus to cause a second instance of said first neuronal event in the subject;

stimulating the subject with a second instance of said second stimulus to cause a second instance of said second neuronal event in the subject, wherein said second instance of said second stimulus occurs at a temporal interval, $\Delta t_{n+1}$, after said second instance of said first stimulus, and wherein said second instance of said first neuronal event and said second instance of said second neuronal event interfere to jointly affect at least one characteristic of a second instance of said first physiological effect at said first region of the subject as a function of said temporal interval, $\Delta t_{n+1}$; and measuring said at least one characteristic of said second instance of said first physiological effect at said first region of the subject.

8. The method of claim 7 further comprising correlating said at least one characteristic of said first physiological effect at said first region as a function of said temporal interval $\Delta t_n$ and said temporal interval $\Delta t_{n+1}$.

9. The method of claim 6 wherein said first stimulus and said second stimulus are the same.

10. The method of claim 6 wherein said first stimulus and said second stimulus are the different.

11. The method of claim 6 wherein the subject is a human being and said first physiological effect comprises hemodynamic and metabolic changes in the subject's brain.

12. The method of claim 6 wherein said measuring is performed with magnetic resonance imaging.

13. The method of claim 6 wherein said at least one characteristic of said first physiological effect comprises the magnitude of said first physiological effect.

14. A method comprising:

(1) stimulating a human being with a first stimulus to cause a first neuronal event in said human being;

(2) stimulating said human being with a second stimulus to cause a second neuronal event in said human being, wherein said second stimulus occurs at a temporal interval, $\Delta t$, after said first stimulus, and wherein said first neuronal event and said second neuronal event each affect the magnitude of a physiological effect at a region in said human being's brain as a function of said temporal interval, $\Delta t$;

(3) measuring the magnitude of the physiological effect at said region in said human being's brain; and (4) repeating steps (1), (2), and (3) while varying said temporal interval, $\Delta t$, to determine which temporal interval, $\Delta t$, causes said first neuronal event and said second neuronal event to interfere and jointly affect the magnitude of the physiological effect at said region in said human being's brain.

15. The method of claim 14 further comprising correlating the magnitude of physiological effect at said region in said human being's brain as a function of said temporal interval, $\Delta t$.

16. The method of claim 14 wherein said first stimulus and said second stimulus are the same.

17. The method of claim 14 wherein said first stimulus and said second stimulus are the different.

18. The method of claim 14 wherein said measuring is performed with magnetic resonance imaging.

19. A method comprising:

(1) stimulating a human being with a first stimulus to cause a first neuronal event in said human being that causes a first physiological effect at a region in said human being's brain;

(2) measuring with magnetic resonance imaging a magnitude of said first physiological effect at said region in said human being's brain caused by said first neuronal event;

(3) repeating steps (1) and (2) until a profile of said first physiological effect is achieved that has a desired statistical significance;

(4) stimulating said human being with said first stimulus to cause said first neuronal event in said human being;

(5) stimulating said human being with a second stimulus to cause a second neuronal event in said human being, wherein said second stimulus occurs at a temporal interval, $\Delta t$, after said first stimulus, and wherein said first neuronal event and said second neuronal event each affect the magnitude of a physiological effect at a region in said human being's brain as a function of said temporal interval, $\Delta t$;

(6) measuring with magnetic resonance imaging the magnitude of the physiological effect at said region in said human being's brain; and (7) repeating steps (4), (5), and (6) while varying said temporal interval, $\Delta t$, to determine which temporal interval, $\Delta t$, causes said first neuronal event and said second neuronal event to interfere and jointly affect the magnitude of the physiological effect at said region in said human being's brain.

20. The method of claim 19 wherein said first stimulus and said second stimulus are the same.

21. The method of claim 19 wherein said first stimulus and said second stimulus are different.

* * * * *